United States Patent [19]

Shvedov et al.

[11] 3,970,707

[45] July 20, 1976

[54] METHOD FOR PREPARING 3,5,3',5'-TETRABROMO-2,4,2',4'-TETRAOXYDIPHENYL

[76] Inventors: Vasily Ivanovich Shvedov, ulitsa M. Ulyanovoi, 9, korpus 3, kv. 11; Alexei Nikolaevich Grinev, Belyaevo-Bogorodskoe, kvartal 44, korpus 9, kv. 57; Evgenia Nikolaevna Sytina, 5 parkovaya ulitsa, 64, korpus 2, kv. 93, all of Moscow, U.S.S.R.

[22] Filed: Apr. 11, 1974

[21] Appl. No.: 460,104

[52] U.S. Cl. ................................................. 260/620
[51] Int. Cl.$^2$........................................ C07C 37/00
[58] Field of Search ........................ 260/620, 621 F

[56] References Cited
UNITED STATES PATENTS

| | | | |
|---|---|---|---|
| 2,735,765 | 2/1956 | Loria et al. | 260/621 F |
| 3,182,088 | 5/1965 | Hennis | 260/620 |
| 3,256,336 | 6/1966 | Lange | 260/621 F |
| 3,752,856 | 8/1973 | Nagy et al. | 260/620 |

*Primary Examiner*—Norman Morgenstern
*Attorney, Agent, or Firm*—Fleit & Jacobson

[57] ABSTRACT

The method for preparing 3,5,3',5'-tetrabromo-2,4,2',4'-tetraoxydiphenyl consists in that 2,4,2',4'-tetramethoxydiphenyl is processed with an acid agent, such as aluminium chloride, aluminium bromide, or hydrogen bromide in acetic acid, in a medium of an organic solvent at a temperature up to 120°C; the obtained 2,4,2',4'-tetraoxydiphenyl is then processed with bromine in a medium of an organic solvent and the end product is finally isolated.

6 Claims, No Drawings

METHOD FOR PREPARING 3,5,3',5'-TETRABROMO-2,4,2',4'-TETRAOXYDIPHENYL

This invention relates to a method for preparing 3,5,3',5'tetrabromo-2,4,2',4'-tetraoxydiphenyl which is used as an active principle in antiviral medicinal preparations and also as a stabilizing agent in the manufacture of polymers.

Known in the prior art are methods for preparing 3,5,3',5'-tetrabromo-2,4,2',4'-tetraoxydiphenyl from bis-(3,5,5-tribromo-4,6-dioxocyclohexene-2-ylidene (tribromoresoquinone) which is prepared by heating 2,4,4,6,6-pentabromocycloxene-1-dione-3,5 (pentabromoresorcinol) at a temperature of 157°–160°C with simultaneous passage of carbon dioxide through the mixture to remove the evolving bromine. The process is usually carried out in an inert solvent at a temperature of 143°–145°C. The obtained tribromoresoquinone is reduced by hydrogen sulphide, tin in dilute hydrochloric acid, hydroxylamine, phenylhydrazine or salts of oxy-acids of sulphur of lower valency (for example, sodium bisulphite in the presence of hydroiodic acid to prepare 3,5,3',5'-tetrabromo-2,4,2',4'-tetraoxydiphenyl.

The disadvantage inherent in the known methods is the complexity of their realization which is due to the thermal decomposition of pentabromoresorcinol which proceeds with vigorous liberation of heat and of large quantities of bromine, which makes it difficult to control the process and involves undue expenditures of bromine and pollution of the end product. The product prepared by the known method is heavily contaminated with pigments and has the melting point at about 280°C. After a series of re-precipitations, the product is a greyish powder melting at temperatures not over 285°C. The chemical flowsheet underlying the known method requires much bromine and offers many process difficulties at considerable loads on the equipment. In order to prepare by the known method one mole of the end product comprising 4 atoms of bromine, 10 moles of bromine are required, of which eight are split off at subsequent stages of the process in the form of free bromine or hydrobromic acid. The debromination step according to the known method should be carried out within a narrow range of temperatures measured by 2°C. (143°–145° C) which is difficult to attain in the conditions of exothermic reaction, whereas the deviation from the required temperature range drastically decreases the yield of the end product.

Another disadvantage of the known method is also high toxicity of the intermediate products, namely of tribromoresoquinone and pentabromoresorcinol which produce marked local irritation on the skin and mucosa, well penetrate intact skin to produce itching, edema and other irritating action.

The main object of the invention is to simplify the process for obtaining the end product.

Another object of the invention is to improve the quality of the end product.

These and other objects have been attained in that in the process for preparing 3,5,3',5'-tetrabromo-2,4,2',-4'-tetraoxydiphenyl, according to the invention, 2,4,2',4'-tetramethoxydiphenyl is processed with acid agents selected from the group, consisting of aluminium chloride, aluminium bromide, and hydrogen bromide in acetic acid, in an organic solvent at a temperature up to 120°C; next the obtained 2,4,2',4'-tetraoxydiphenyl is processed with bromine in a medium of an organic solvent and finally the end product is isolated.

It is reasonable to use absolute benzene, toluene, xylene, acetic acid, methylene chloride and carbon disulphide as the organic solvent for treating 2,4,2',4'-tetramethoxydiphenyl with acid agents. The acid-processing should be done at temperatures within the range from 80° to 120°C.

The obtained 2,4,2',4'-tetraoxydiphenyl, should preferably be processed in an organic solvent, such as dioxane, acetic acid or methylene chloride.

The obtained 2,4,2',4'-tetraoxydiphenyl should be processed with bromine taken in stoichiometric quantity.

The proposed method can be realized as follows.

The starting product 2,4,2',4'-tetramethoxydiphenyl is processed with acid agents, such as aluminium chloride, aluminium bromide, or hydrogen bromide in acetic acid.

The starting product 2,4,2',4'-tetramethoxydiphenyl can be prepared by the Ulmann reaction by treating 1,3-dimethoxy-4-iodobenzene with powdered copper, with heating, according to the following equation

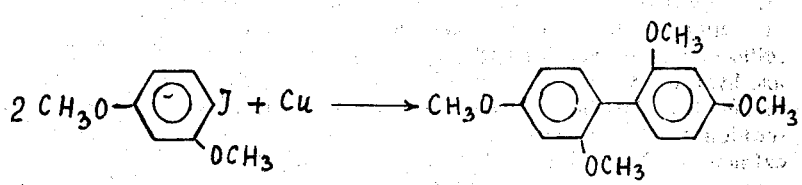

The acid treatment of 2,4,2',4'-tetramethoxydiphenyl should be done at temperatures to 120°C, preferably at temperatures from 80° to 120°C.

It is recommendable to use absolute benzene, toluene, xylene, acetic acid, methylene chloride or carbon disulphide as an organic solvent. The prepared 2,4,2',-4'-tetraoxydiphenyl is reacted with bromine at room temperature, in the presence of organic solvents, for example, dioxane, methylene chloride, or acetic acid. The end product is then isolated.

This method simplifies significantly the process flowsheet, excludes the step of pyrolysis of pentabromoresorcinol and reduces consumption of bromine. The end product obtained according to the proposed method is a white, slightly pinkish crystalline substance melting at 289°C.

An important advantage of the proposed method is that the product obtained by the novel method does not contain pigments or other extraneous admixtures as early as at the stage of technical product, moreover it is no longer necessary to deal with highly toxic intermediate substances that are otherwise formed in the known processes.

For a better understanding of the invention, the following examples of its practical embodiment are given by way of illustration.

EXAMPLE 1

A mixture of 2.5 g (0.0092 mole) of 2,4,2',4'-tetramethoxydiphenyl, 10 ml of absolute benzene and 8.3 g (0.062 M of aluminium chloride is boiled with a reflux condenser, under stirring, for three hours. Then 15 ml of absolute benzene are added to the reaction mixture, the mixture is stirred thoroughly and poured into crushed ice containing 3 ml of concentrated hydrochloric acid which is required to decompose the aluminium chloride complex. The benzene layer is separated, washed with water, with a saturated solution of sodium bicarbonate, then again with water, after which benzene is removed by distillation to give 1.35 g (67.5 per cent by weight) of 2,4,2',4'-tetraoxydiphenyl. M.p. 225°–226°C (from water).

To a solution of 0.4 g (0.00183 mole) of 2,4,2',4'-tetraoxydiphenyl in 20 ml of acetic acid, at a temperature of 25°C added dropwise with stirring are 0.4 ml (0.0077 mole) of bromine in 2 ml of acetic acid. The reaction mixture becomes hot, its temperature rises to 32°C. As soon as the specified quantity of bromine is all added, the clear solution is stirred for another thirty minutes, (crystals begin precipitating already in ten minutes). The reaction mixture is cooled, the crystals are separated on a filter and the end product is thus obtained (0.77 g). As the mother liquor is evaporated under vacuum, another portion of the end product (0.16 g) is recovered. The total yield of 3,5,3',5'-tetrabromo-2,4,2',4'-tetraoxydiphenyl is 0.93 g (94.9 per cent by weight); its melting point is 286°–287°C.

EXAMPLE 2

A mixture of 4 g (0.0146 mole) of 2,4,2',4'-tetramethoxydiphenyl, 100 ml of acetic acid and 80 ml of a 48 per cent solution of hydrobromic acid is boiled with a reflux condenser on an oil bath for 6 hours. Then acetic and hydrobromic acids are distilled under vacuum, the remaining dry residue is dissolved in water, the aqueous solution is extracted with ether (4 × 50 ml), the ether extract is washed with a small portion of water and then extracted with a 5 per cent solution of sodium hydroxide (4 × 50 ml), and finally two times with water. The collected aqueous-alkaline extract is cooled, acidified with dilute (1:1) hydrochloric acid to a weak reaction to congo, and extracted with ether (4 × 50 ml). The ether extract is filtered through activated carbon, dried with sodium sulphate and after removal of ether, obtained are 2.37 g (74.5 per cent by weight) of 2,4,2',4'-tetraoxydiphenyl. The melting point of the product is 226°–227°C (from water).

To a suspension of 0.4 g (0.00183 mole) of 2,4,2',4'-tetraoxydiphenyl in 30 ml of methylene chloride added dropwise, at room temperature with stirring, is 0.4 g (0.0077 mole) of bromine in 2 ml of methylene chloride. As soon as bromine is all added, the reaction mixture is stirred for another hour, the end product separated on a filter. The yield is 0.81 g (83 per cent by weight). As the mother liquor is evaporated under vacuum, another portion of 0.11 g of the end product is recovered, and the total yield of 3,5,3',5'-tetrabromo-2,4,2',4'-tetraoxydiphenyl is 0.92 g (94 per cent by weight); the melting point is 288°–289°C. The product is a white, slightly pinkish, crystalline substance.

EXAMPLE 3

A mixture of 5 g (0.0184 mole) of 2,4,2',4'-tetramethoxydiphenyl, 40 ml of anhydrous methylene chloride and 16.6 g (0.122 mole of aluminium chloride is boiled with a reflux condenser, with stirring, for 4 hours. Added to the reaction mixture is another portion of 50 ml of methylene chloride and the flask contents are poured onto crushed ice containing 100 ml of a 3N solution of hydrochloric acid. The organic layer, obtained after decomposition of the aluminium chloride complex, is washed in a dividing funnel with water, a saturated aqueous solution of sodium bicarbonate, the solvent is removed by distillation and finally 4.7 g (74 per cent by weight) of 2,4,2',4'-tetraoxydiphenyl are obtained. The melting point of the product is 226°–227°C (from water).

To a solution of 0.4 g (0.00183 mole) of 2,4,2',4'-tetraoxydiphenyl in 10 ml of dioxane added is within a period of time of 20 minutes (at room temperature and with stirring) 0.47 ml (1.23 g, 0.0077 mole) of bromine in 2 ml of acetic acid. The reaction solution is stirred for another 20 minutes then it is transferred into a distillation flask and evaporated to dryness under vacuum (water-jet ejector) with heating on a water bath. The yield is 0.92 g (94 per cent of 3,5,3',5'-tetrabromo-2,4,2',4'-tetraoxydiphenyl; m.p., 285°C.

Found in per cent: C, 26.90; 27.29; H, 1.25; Br, 59.74; 59.49; $C_{12}H_6Br_4O_4$. Calculated, in per cent: C, 26.99; H, 1.13; Br, 59.88.

EXAMPLE 4

To a solution of 5 g (0.0184 mole) of 2,4,2',4'-tetramethoxydiphenyl in 50 ml of carbon disulphide added swiftly with stirring is a solution of 33.1 g of aluminium bromide in 250 ml of carbon disulphide. The mixture is boiled with stirring for 1 hour. Then, to the cooled reaction mixture added are 100 g of crushed ice, 200 ml of a 3N solution of hydrochloric acid and 200 ml of ether. The components are mixed for one hour and transferred into a dividing funnel. The organic phase is separated, washed with water, a saturated aqueous solution of sodium bicarbonate, and dried with sodium sulphate. The solvent is then removed by distillation to give 4.6 g of 2,4,2', 4'-tetraoxydiphenyl, melting at 226°–227° (from water).

To the a suspension of 0.4 g (0.00183 mole) of 2,4,2',4'-tetraoxydiphenyl in 30 ml of methylene chloride added dropwise at room temperature with stirring is 0.4 g (0.0077 mole) of bromine in 2 ml of methylene chloride. As soon as bromine is all added, the reaction mixture is stirred for another hour and the precipitate is separated on a funnel. The yield is 0.81 g (83 per cent by weight) of the end product. As the mother liquor is evaporated under vacuum another portion of 0.11 g of the product is recovered and the total yield of 3,5,3',5'-tetrabromo-2,4,2',4'-tetraoxydiphenyl is thus 0.92 g (94 per cent by weight). The melting point, 288°–289°C. The product is a white, slightly pinkish crystalline substance.

What we claim is:

1. A method which comprises reacting 2,4,2',4'-tetramethoxydiphenyl with an acid agent selected from the group consisting of aluminium chloride, aluminium bromide, and hydrogen bromide in acetic acid in the presence of an organic solvent at a temperature up to 120°C, separating 2,4,2',4'-tetraoxydiphenyl from the reaction mixture and reacting the separated product with bromine in the presence of an organic solvent to form 3,5,3',5'-tetrabromo-2,4,2',4'-tetraoxydiphenyl, and recovering the end product.

2. The method of claim 1 in which said 2,4,2',4'-tetramethoxydiphenyl is reacted with said acid agent in the presence of an organic solvent selected from the group consisting of absolute benzene, toluene, xylene, acetic acid, methylene chloride and carbon disulphide.

3. The method of claim 1 in which said temperature is 80° to 120°C.

4. The method of claim 1 in which said 2,4,2',4'-tetraoxydiphenyl is reacted with bromine in the presence of an organic solvent selected from the group consisting of dioxane, acetic acid and methylene chloride.

5. The method of claim 1 in which said 2,4,2',4'-tetraoxydiphenyl is reacted with a stoichiometric quantity of said bromine.

6. A method which consists essentially of reacting 2,4,2',4'-tetramethoxydiphenyl with an acid agent selected from the group consisting of aluminium chloride, aluminium bromide, and hydrogen bromide in acetic acid in the presence of an organic solvent selected from the group consisting of absolute benzene, toluene, xylene, acetic acid, methylene chloride and carbon disulphide at a temperature of 80° to 120°C, separating 2,4,2',4'-tetraoxydiphenyl from the reaction mixture and reacting the separated product with a stoichiometric quantity of bromine in the presence of an organic solvent selected from the group consisting of dioxane, acetic acid and methylene chloride to form 3,5,3',5'-tetrabromo-2,4,2',4'-tetraoxydiphenyl and recovering the end product.

* * * * *